United States Patent [19]

Kensey et al.

[11] Patent Number: 4,679,558
[45] Date of Patent: Jul. 14, 1987

[54] CATHETER BASED SURGICAL METHODS AND APPARATUS THEREFOR

[75] Inventors: Kenneth Kensey, Hinsdale, Ill.; John Nash, Downingtown, Pa.

[73] Assignee: Intravascular Surgical Instruments, Inc., Telford, Pa.

[21] Appl. No.: 909,802

[22] Filed: Sep. 22, 1986

Related U.S. Application Data

[62] Division of Ser. No. 765,034, Aug. 12, 1985.

[51] Int. Cl.⁴ .............................................. A61B 17/00
[52] U.S. Cl. ................................. 128/328; 128/303.15
[58] Field of Search .................... 128/303.15, 319, 328, 128/305

[56] References Cited

U.S. PATENT DOCUMENTS 4,227,532 10/1980 Bluhm et al. .................... 128/328
4,589,412 5/1986 Kensey .......................... 128/304 X Primary Examiner—Stephen F. Husar
Attorney, Agent, or Firm—Caesar, Rivise, Bernstein, Cohen & Pokotilow, Ltd.

[57] ABSTRACT

Methods for effecting various surgical procedures via the use of a flexible, small diameter, catheter. The catheter includes a working head arranged to be moved, e.g., rotated, at a high rate of speed by an associated drive system. In one method the catheter with the moving head is brought into engagement with a restriction caused by an atherosclerotic deposit in an artery to effect the opening of the restriction by the dilation of the artery. In another method the catheter is used to dilate a duct or tube, e.g., a fallopian tube, eustachian tube, bile duct, etc. in a living being. In another application the catheter is used to effect the in situ valvulectomy of a section of vein within a living being. In still another method the catheter is used to disintegrate a stone, such as a kidney or gall stone, in the body of a living being. In yet another method, the catheter is used to stop spasm in a lumen in a living being. A catheter is also disclosed which is particularly configured to effect an in situ valvulectomy or stone disintegration procedure.

23 Claims, 14 Drawing Figures

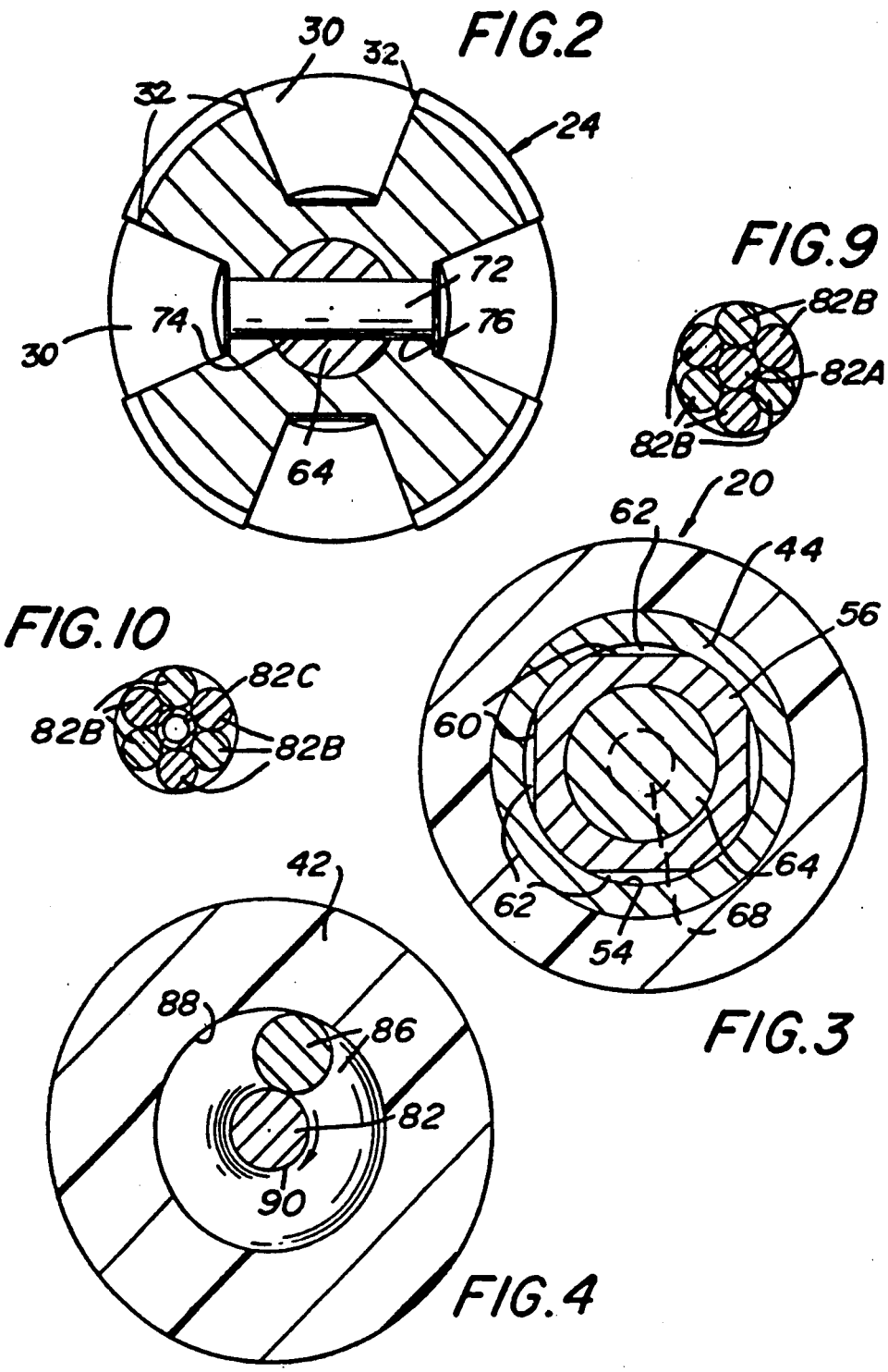

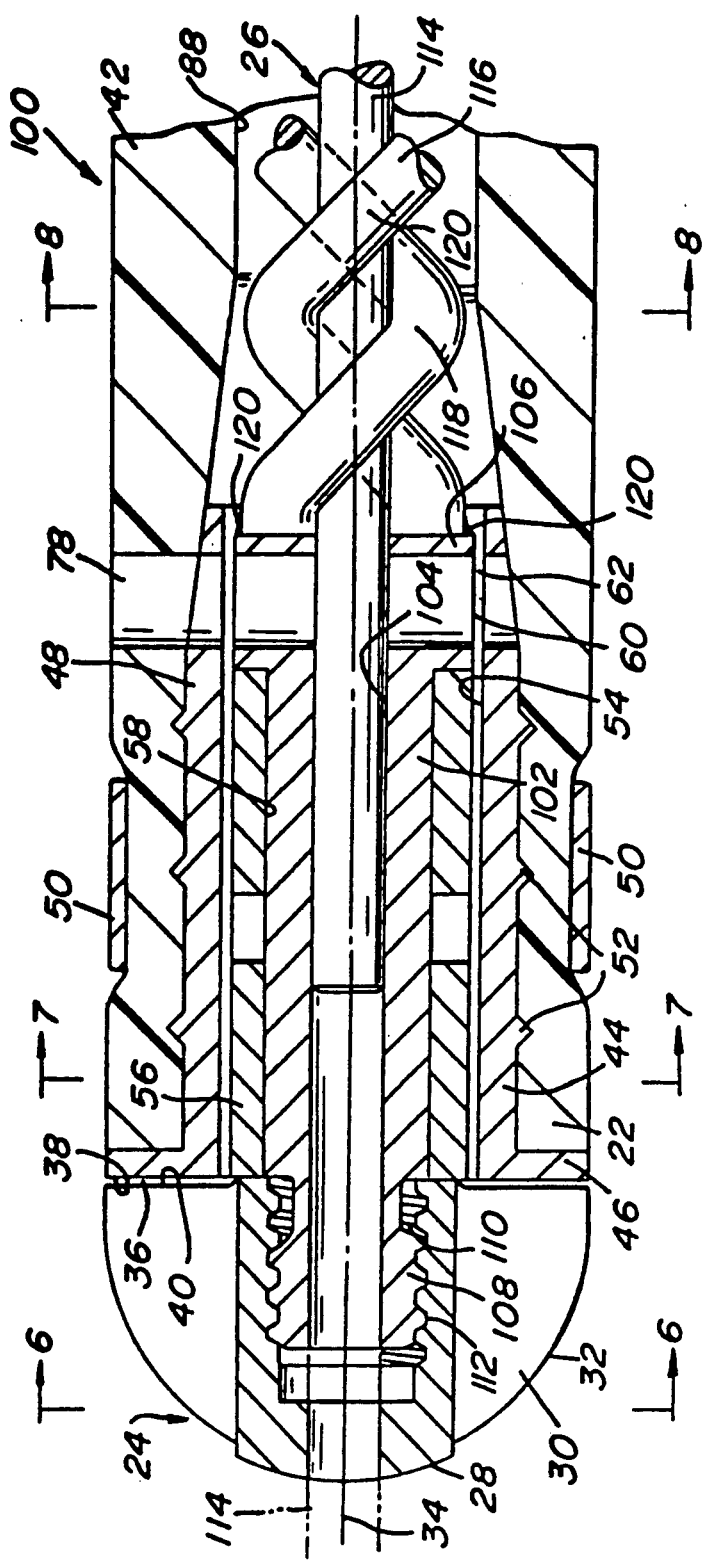

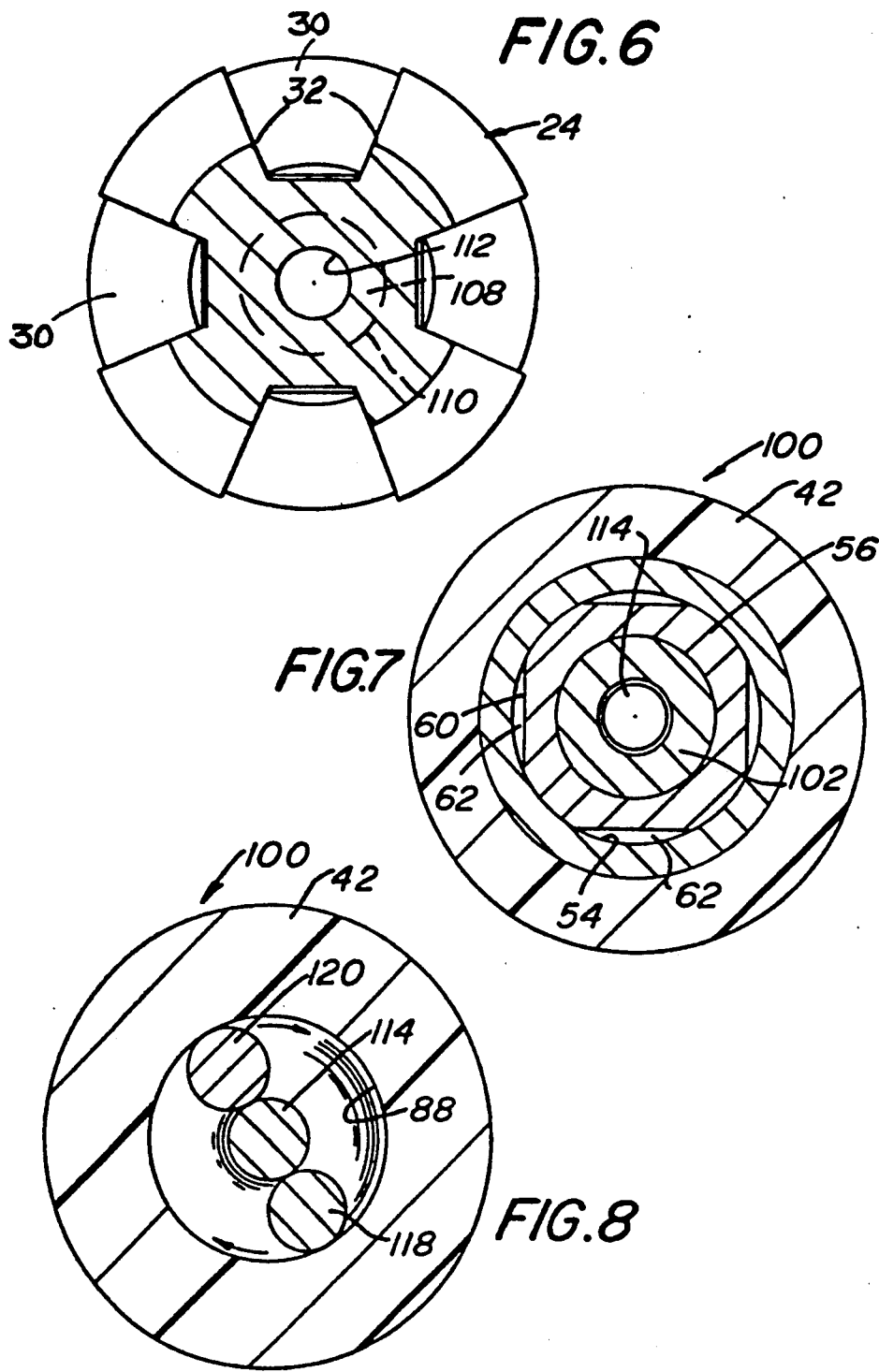

CATHETER BASED SURGICAL METHODS AND APPARATUS THEREFOR

This application is a division of pending application Ser. No. 06/765,034, filed Aug. 12, 1985.

BACKGROUND OF THE INVENTION

This invention relates generally to medical devices and more particularly to flexible, power driven catheters for intravascular surgery and other medical surgery and procedures.

In U.S. Pat. No. 4,445,509 (Auth) there is disclosed a recanalization catheter for cutting away hard abnormal deposits, such as atheroscleratic plaque, from the inside of an artery and while preserving the soft tissue thereof. That recanalization catheter includes a multi-fluted, rotary cutting head mounted at the distal end of the catheter and arranged to be rotated by a flexible drive shaft extending down the center of the catheter. The rotation of the cutting head is stated as producing differential cutting to effect the removal of relatively hard deposits from relatively soft tissue. The drive shaft is arranged to be rotated within the catheter by an electric motor coupled to the proximal end thereof. The drive shaft is disclosed as being a steel helical coil of approximately 0.05 inch (1.3 mm) diameter. Such a coil is stated in the patent to be successful in transmitting high rotational speed (greater than 25,000 rpm) in a controlled fashion and with mechanical security.

In order for a recanalizing catheter to have wide applicability of use in intravascular surgery, its length should be sufficiently large, e.g., 2 to 3 feet or more, while its outside diameter, at least adjacent the working end, is sufficiently small, e.g., 3-4 mm. Moreover the catheter should be able to bend through a minimum diameter radius of curvature of 3 inches or less, in order to reach small, remotely located restrictions, e.g., occlusions.

As will be appreciated by those skilled in the art the torsional shear stress produced on a flexible drive shaft (e.g., a wire) will differ for different composition wires, e.g., approximately 150,000 psi for steel wires, 70,000 psi for beryllium-copper wires. If the radius of curvature through which the drive shaft must bend is very small, e.g., less than 3 inches, high bending stresses will be induced therein. In order to reduce bending strain the diameter of the flexible drive shaft or wire must be made very small, e.g., 0.02 or less inches. If the restriction opening tool is to operated at a high rate of speed, e.g., greater than 20,000 rpm, in order to provide sufficient power at low torque, the deleterious dynamic effects of critical whirl (e.g., undue vibration) and friction caused by high side loads on the bearing surfaces supporting the drive wire must be overcome or minimized while the positional neutrality (centering) of the drive shaft is maintained in order to insure that proper operation ensues. Flexible drive systems of the prior art appear to leave much to be desired from the standpoint of effectiveness and efficiency of operation in applications involving high speed, small diameter, and small radius of curvature.

In copending U.S. patent application Ser. No. 06/701,063, filed on Feb. 13, 1985, entitled Shaft Driven, Flexible Intravascular Recanalization Catheter, which application is assigned to the same assignee as this invention, and whose disclosure is incorporated by reference herein there is disclosed and claimed a flexible drive assembly for use with recanalization catheters which overcomes the above noted disadvantages of the prior art. To that end the drive assembly as set forth in that application is a flexible assembly which is arranged to be disposed within a very small diameter, elongated, flexible tubular member having a distal end at which a tool, e.g., a cutter, is mounted for high speed rotation. The drive assembly includes a flexible drive shaft, e.g., a continuous length solid bodied or tubular wire or group of wires, which is mounted within plural spaced bearings to enable it to be rotated at a very high rate of speed from a remotely located motor. The bearings each basically comprise ball-like members having a central opening through which the drive shaft extends. The ball-like bearing members are spaced apart by plural spacer elements at a distance no greater than one-half the wave length of the standing wave which would naturally result from the rotation of a correspondingly sized but unsupported wire at the rotational speed. Each spacer element basically comprises an elongated tubular member having a pair of flared ends. Each of the ball-like bearing members is located between the trailing flared end of one spacer member and the leading free end of the next succeeding, proximally located spacer. Thus, the bearings and associated spacers serve to keep the drive shaft centered even as the catheter is bent through a sharp radius of curvature, while also preventing the shaft from going into critical whirl. A cooling fluid is preferably provided throughout the interior of the tubular member to cool and lubricate the bearings and driveshaft.

While the invention disclosed and claimed in the above noted copending application is suitable for its intended purposes, it is nevertheless somewhat complex in construction. Hence a need existed for a flexible drive shaft having a simple and inexpensive bearing system for supporting an elongated rotary drive element at a central or neutral position while the production of undue or excessive vibration which could interfere with the restriction opening procedure and resulting from critical whirl.

To that end in copending U.S. patent application Ser. No. 06/746,220, filed on June 19, 1985 entitled Spiral Wire Bearing For Rotating Wire Drive Catheter, which application is assigned to the same assignee as this invention and whose disclosure is incorporated by reference herein, there is disclosed and claimed catheters for introduction in a lumen in a living being to perform a procedure therein. Each catheter is an elongated flexible member having a distal end at which a working head is located. The working head is preferably rotary and is arranged to be rotated by a drive assembly. The drive assembly includes elongated drive means for the working head and which extends through the catheter from the working head to a first remote, proximal location. The drive assembly also includes elongated bearing means which extends within the catheter from a point adjacent the working head to a second remote, proximal location. One of the drive means or the bearing means is formed as a spiral of at least one wire wrapped about the other of said means, whereupon the drive means can be rotated freely with respect to the other means and to the catheter to effect the rotation of the working head. The drive means and the bearing means cooperate with each other to maintain the drive means at a neutral position within the catheter as the catheter is bent through any arc up to a minimum radius of curvature, while enabling the drive means to be rotated at a high rotational speed without resulting in undue vibration which would interfere with the procedure, e.g., artery revascularization, being carried out by the catheter.

Various United States patents related to powered drive shafts, particularly flexible drive shafts and including spirally wound bearings. For example, U.S. Pat. No. 3,180,625 (Wyzenbeek) discloses a flexible shaft having an outer casing enclosing a rotating core and providing a mouth for a spirally wound bearing. The bearing includes a rib for supporting the rotating core. U.S. Pat. No. 4,112,708 (Fukuda) discloses a flexible drive cable having a rotary flexible core member formed of plural strands. The core is supported in a tubular elongated liner member. In some embodiments the liner member is in the form of spirally disposed surfaces to provide plural lubrication grooves therebetween. U.S. Pat. No. 1,785,345 (Hasemann) discloses an elongated flexible shaft such as used with an automobile speedometer located within a casing forming a bearing for the shaft. The cable is supported by a strip formed in a spiral and made of a wear-resisting hard metal. U.S. Pat. No. 2,821,092 (Cordoro et al.) discloses a rotary drive cable to which is fixedly secured a spiral element. The element serves to hold and position the central core within a liner and is formed of Teflon.

While the devices in all of the foregoing patents may be suitable for their intended purposes, none appears suitable for high speed operation in confined, small radius of curvature applications, where drive element positional neutrality and resistance to vibration, (such as would be caused by critical whirl), is of major importance, such as exists in artery revascularization, and other surgical procedures.

Other prior art devices utilizing flexible drive shafts for conveying rotary power to a working head or tool are disclosed in the following U.S. Pat. Nos.: 1,481,078 (Albertson), 1,636,038 (Bolozsky et al.), 2,570,335 (Fitch), 2,761,297 (Buchsteiner et al) and 4,424,045 (Kulischenko et al).

In copending U.S. patent application Ser. No. 06/567,506, filed on Jan. 3, 1984 which is now U.S. Pat. No. 4,589,412, entitled Method and Apparatus for Surgically Removing Remote Deposits, which has been assigned to the same assignee as this invention and whose disclosure is incorporated by reference herein, there is disclosed and claimed a fluid powered flexible catheter for opening restriction, such as caused by atherosclerotic plaque, in blood vessels of living beings. Further aspects of that invention are disclosed and claimed in copending Continuation-in-Part Application Ser. No. 06/682,393, which is now U.S. Pat. No. 4,631,052, filed on Dec. 17, 1984, entitled Method and Apparatus for Surgically Removing Remote Deposits, also assigned to the same assignee as this invention and whose disclosure is also incorporated by reference herein.

The catheters of all of the foregoing copending and coassigned patents are not only suitable for intravascular recanalization procedures, but also may be used to effect other important medical/surgical procedures as well. Thus, among the procedures for which said catheters can be utilized are the following: peripheral and coronary vascular recanalization via removal of plaque and/or dilatation of the blood vessel, dilatation of small bodily lumens, such as eustachian or fallopian tubes, removal of thrombi, destruction of stones, such as gall stones, kidney stones, bile stones, etc., and in situ valvulectomy. Those methods and catheters for carrying out those methods constitute the subject matter of this application.

OBJECTS OF THE INVENTION

Accordingly, it is a general object of this invention to provide methods of performing various medical/surgical functions with the use of flexible catheters and which overcome the disadvantages of the prior art.

It is a further object of this invention to provide a method of opening a restriction or stricture in a lumen of a living being by effecting the dilation thereof via use of a flexible catheter.

It is a further object of this invention to provide a method of opening a restriction in a blood vessel by effecting the dilation thereof via use of a flexible catheter.

It is still a further object of this invention to provide a method of dilating a duct or tube, such as a fallopian tube or a eustachian tube, within a living being via use of a flexible catheter.

It is yet a further object of this invention to provide in situ a method of rendering valves in a vein inoperative via use of a flexible catheter.

It is yet a further object of this invention to provide a method of disintegrating a stone or any loose hard body located within the body of a living being, such as a kidney stone, gall stone, bile stone, etc., via use of a flexible catheter.

It is yet a further object of this invention to provide a flexible catheter for use in performing the valvulectomy and stone disintegration process of this invention.

SUMMARY OF THE INVENTION

These and other objects of the instant invention are achieved by providing a method of performing a medical/surgical procedure within the body of a living being and utilizing an elongated, small diameter, flexible catheter. The catheter has a longitudinal axis and a working head located at the distal end thereof. The working head is arranged for high speed movement with respect to the axis by associated drive means. The drive means is arranged to effect the movement of the working head even if the catheter is bent through an arc up to a minimum radius of curvature and without resulting in excessive vibration which could interfere with the procedure.

In accordance one aspect of the invention the method comprises increasing the diameter of a lumen within the body of the living being. To that end the method entails inserting the catheter into the lumen from a remote location and operating the drive means to cause the working head to move at the high rate of speed. The catheter is advanced into the lumen along the longitudinal axis as the working head is moving, whereupon the mechanical action of the working head causes the lumen to be enlarged. The lumen may be a blood vessel having a restriction therein caused by some material, e.g., atherosclerotic plaque, or may be a constricted duct, tube, or other passageway, e.g., a fallopian tube.

In accordance with another aspect of the invention the method comprises rendering the valves in a section of vein inoperative in situ. To that end that method entails inserting the catheter into the vein section from a remote location, operating the drive means to cause the working head to move at a high rate of speed. The catheter is advanced into the vein as the working head is moving so that it contacts the valve, whereupon the mechanical action of the working head renders the valve inoperative.

In accordance with yet another aspect of the invention the method comprises disintegrating a stone or other loose body (e.g., a body containing calcium) located within a living being. To that end that method entails inserting the catheter into the body from a remote location and operating the drive means to cause the working head to move at the high rate of speed. The catheter is advanced into the lumen along the longitudinal axis as the working head is moving, until it is brought into contact with the stone, whereupon the mechanical action of the working head pulverizes the stone to result in its disintegration.

In accordance with yet another aspect of the invention there is provided a catheter for use in the stone disintegration process or valvulectomy process. That apparatus comprises an elongated, small diameter, flexible catheter having a longitudinal axis and a distal end at which a working head is located. The working head is arranged for high speed movement with respect to the axis by drive means located within the catheter. The drive means is arranged to freely effect the movement of the working means even if the catheter is bent through any arc up to a minimum radius of curvature and without resulting in excessive vibration which could interfere with the process. The working head comprises portions adapted to impact the stone or valve at a high rate of speed to effect the pulverization and/or destruction thereof.

DESCRIPTION OF THE DRAWING

Other objects and many of the attendant advantages of the instant invention will become readily appreciated when the same becomes better understood by reference to the following detailed description when considered in connection with the accompanying drawing wherein:

FIG. 2 is a sectional view taken along line 2—2 of FIG. 1;

FIG. 3 is a sectional view taken along line 3—3 of FIG. 1;

FIG. 4 is a sectional view taken along line 4—4 of FIG. 1;

FIG. 5 is a side elevational view, partially in section, showing the distal end of an alternative catheter device for carrying out the methods of this invention;

FIG. 6 is a sectional view taken along line 6—6 of FIG. 5;

FIG. 7 is a sectional view taken along line 7—7 of FIG. 5;

FIG. 8 is a sectional view taken along line 8—8 of FIG. 5.

FIG. 9 is an enlarged sectional view of an alternative embodiment of a drive wire or guide wire for a catheter for carrying out the methods of this invention;

FIG. 10 is an enlarged sectional view of yet another alternative embodiment of a drive wire or guide wire for a catheter for carrying out the methods of this invention.

DETAILED DESCRIPTION OF THE PREFERRED EMBODIMENT

Figure 1:
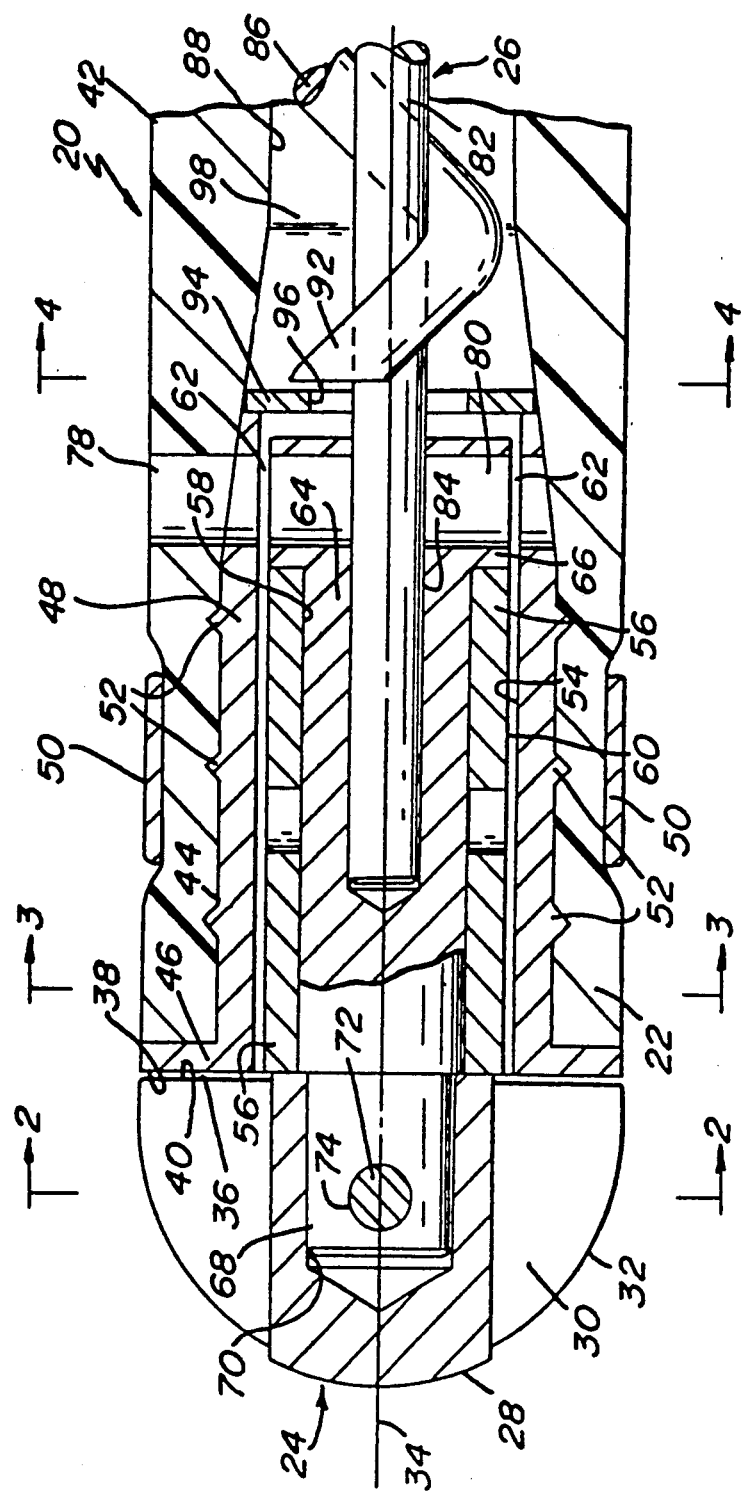
FIG. 1 is a side elevational view, partially in section, showing the distal end of a catheter for carrying out the methods of this invention.

Referring now in greater detail to the various figures of the drawing wherein like reference characters refer to like parts, there is shown at 20 in FIG. 1 the distal end of a recanalizing catheter 20 for intravascular or other surgical applications, e.g., fallopian tube dilation. The catheter 20 includes a flexible drive assembly constructed in accordance with this invention. That drive assembly will be described in considerable detail later and is particular suited for in body surgical applications, but can be use for other applications requiring the transmission of power at high speed and low torque through a very narrow path including bends of small (minimum) radius of curvature, e.g., 3 inches (7.62 cm). The catheter 20 is an elongated, flexible device, having a distal end portion 22 at which a working head or tool 24 is mounted, and a proximal end portion (not shown) which is adapted to be connected to a source of rotary power, e.g., an electric motor (not shown). The catheter 20 includes the heretofore mentioned drive assembly, now designated by the reference numeral 26, and which extends the length of the catheter to drive, e.g., rotate, the working head under the power provided from the remote power source (motor).

In one use, catheter 20 is introduced into the vascular system of the patient such as through an opening in the femoral artery at the point in the groin of the patient remote from the site of the vascular occlusion or blockage that has been determined to exist in an artery, e.g., a coronary artery. The catheter is then passed via the aorta into the heart and then into the desired coronary artery to the point at which the working head is located immediately adjacent the restriction, e.g., partial occulsion or full occulsion. As will be recognized by those skilled in the art such restrictions are formed by the deposit of atherosclerotic plaque or some other material(s), such as waxy and/or calcified atheroma, thickened and/or ulcerated intima, etc.

In the catheter embodiment shown herein the working head or tool 24 comprises a rotary cutter. The cutter is mounted at the distal end of the drive assembly. The cutter basically comprises a solid bodied element of whose outer surface 28 is of generally convex shape and which is provided with four recesses 30 therein. The intersection of each of the walls of each recess 30, with the convex surface of the cutter, forms an arcuate cutting edge or blade 32. In accordance with the preferred embodiment of the cutter each arcuate blade 32 includes at least one surface portion having zero or negative rake, with the rake being preferably negative at an angle of approximately 10° to 30°.

The cutter head 24 is arranged to be rotated at a high rate of speed, e.g., in excess of 20,000 rpm, about the longitudinal central axis 34 of the catheter under power provided from the remote power source, via the flexible drive assembly 26. In order to cool and lubricate the drive assembly a fluid, e.g., water or an oxygenated liquid, is passed through the interior of the catheter from an entrance point adjacent the proximal end thereof. Moreover, the fluid is arranged to exit from the catheter at the distal end 22 thereof through a narrow interface 36 formed between the distal end surface 38 of the catheter itself and the proximal face of the cutter head 24. The exiting fluid has the advantageous effect of providing positive pressure to the wall of the artery contiguous with the cutter 24. In addition the flow of fluid outward through the interface 36 also precludes fine fiberous tissue of the artery from gaining ingress into the interface where it could snag or spool-up. Moreover, the rotating cutter blades impart momentum to the exiting fluid, which action applies further positive pressure to the artery wall, thereby further decreasing the chances of tissue-snagging.

The restriction opening process is carried out by advancing the catheter 20 as the cutter head 24 rotates into the material making up the restriction so that the rotating head engages that material. In the aforementioned copending application Ser. No. 06/746,220 the manner in which the restriction opening process is effected was described as follows: "In some instances, e.g., hard or calcified deposits, an opening in the restriction is created by the rotating cutter blades actually cutting away or emulsifing particles of the material(s) making up the restriction. In other instances, e.g., waxy or soft deposits, the material(s) of the restriction may merely be mechanically agitated, beaten, stretched or otherwise disturbed by the blades of the rotating cutter, whereupon an opening is created in the restriction by the movement of the material(s) without such material(s) actually being cut-up or removed from the restriction". Such explanations may be too simplistic. To that end based on additional testing and development conducted since the filing of that application, it has been determined that while the moving working head does, in fact, cause the enlargement or dialation of the opening through which the blood may flow more freely, the exact physiologic reaction of the vessel (lumen) to the action of the head 24 is unknown at this time. What is known is that the walls of the blood vessel itself become dilated and remain dilated even after the catheter and its working head is withdrawn. In particular it has been determined by angiogram and other testing procedures that after one has passed the working head of the catheter past the restriction in accordance with the method of this invention that the wall of the artery has become stretched or dilated and remains such. More particularly it has been found that the adventitia and media portions of the artery are stretched while the intima (lining portion, which is most commonly the diseased portion) is fractured and fissured. Such action ensures that the restriction is thus "opened" to freer blood flow therethrough. Based on experience with balloon angioplasty the fracturing or fissuring of the intima enables renewed blood flow and natural bodily processes to remodel and shrink the lesion in many cases.

Among the factors which may play a part in the restriction opening process is the changing or rearrangement of the vessel structure (e.g., vessel fibers, etc.) due to any one or more of the following: mechanical stretching of the lumen structure resulting from the size of the working head (a static effect) and/or the dynamic effect of cyclical high speed mechanical movement (e.g., rotation) of the working head; increase in temperature of the lumen structure resulting from the mechanical cycling of the viscoelastic properties of the lumen tissue; bombardment with liquid propelled at the lumen wall by the rapid movement (e.g., rotation) of the working head, whereupon the head pressure of the liquid impacting the walls exceeds the normal local blood pressure; forcing or wedging of liquid into the lumen walls by mechanically induced film pressure as the working head's blades slide over the lumen surface, whereupon the tissue fibers are forced apart; and forcing of liquid into the lumen walls by the local dynamic or hydrostatic pressure induced by the injected liquid and/or the moving working head. Other, as yet undetermined factors may also play a part in the dialation process.

In view of the foregoing it must be made clear that any use of the term cutter, cutter head, cutter blade, etc., as used herein merely refers to the structure of the component, and its mode of operation may not, in fact, involve any actual cutting whatsoever.

The details of one preferred catheter 20 for performing intralumen surgical procedures or the other methods of this invention will now be described. As can be seen the catheter 20 basically comprises an elongated, flexible tubular member 42 which is formed of a suitable material, e.g., plastic, and which has a small outside diameter. In the preferred embodiment shown herein the outside diameter is approximately 3 mm (10 French) or less, while the inside diameter of the catheter tube is approximately 1.5 mm (5 French). At the distal end 22 of the catheter tube 42 there is secured a sleeve-like outer bushing 44. The outer bushing forms one portion of the mount for the cutter 26. The bushing 44 is in the form of a distal flanged portion 46 and an elongated tubular body portion 48. The flanged portion 46 forms the distal end of the catheter and in particular the distal surface portion 38 described heretofore. The elongated tubular portion 48 of the bushing extends within the distal end of the catheter tube 42 and is held in place by the use of a retaining band 50. Thus, the retaining band 50 tightly encircles the periphery of the catheter tube 42 to cause plural gripping teeth 52 in the periphery of the bushing portion to dig into the interior surface of the catheter tube and thereby hold the bushing tightly in place therein. Disposed within the central passageway 54 of the outer bushing 44 is an inner bushing 56. The inner bushing 56 is fixedly mounted within the outer bushing 44 and is also formed of a tough, wear resistant, yet low friction material, such as beryllium-copper.

As can be seen in FIGS. 1 and 3 the inner bushing 56 is an elongated member having a central circular passageway 58 extending therethrough. The outer periphery of the inner bushing 56 is of generally circular profile but includes four, equadistantly spaced flatted surface portions 60 (FIG. 3). Each surface portion extends the full length of the inner bushing 56 so as to define a space 62 between it and the cylindrical interior surface of the outer bushing 44. Each of the spaces 62 is in communication with the open interface 36 between the cutting head and the distal end of the catheter to serve as passageway for carrying liquid from the interior of the catheter out through the interface 36 for the reasons described heretofore. As will be described later this liquid also serves to cool and lubricate the moveable members of the flexible drive assembly 26 to facilitate operation of the catheter.

A cutter-mounting shaft 64 is located within the central bore 58 in the inner bushing 56 and extends along its central axis 34 and is arranged to fully rotate within the inner bushing about axis 34. As can be seen the shaft 64 includes a flanged proximal end 66 and a reduced diameter distal end 68. The distal end 68 extends beyond the distal end 38 of the catheter for disposition and securement within a mating central bore 70 in the cutter tip 24.

The cutter tip is fixedly secured to the distal end of the mounting shaft 64 via a retainer pin 72 extending through aligned holes 74 and 76 in the cutter tip mounting shaft 64 and cutter tip 24, respectively, (FIG. 2).

A spragging port 78 extends through the catheter tube sidewall 42. An associated spragging port 80 is provided in the flanged portion 66 of the cutter tip mounting shaft 64. The spragging port 80 extends diametrically with respect to the flange 66 so that it can be aligned with spragging port 78 to lock the rotary position of the tip 24 with respect to the catheter, when such action is desired, e.g., during maintenance and adjustment of the device.

The flexible drive assembly 26 basically comprises an elongated drive wire or shaft 82 which extends the length of the catheter from the remote, proximally located power source to the cutter tip mounting shaft 64. The drive shaft 82 is secured to the cutter tip mounting shaft 64. In particular the distal end of the drive shaft 82 extends into a central bore 84 therein and is fixedly secured in place in the bore 84 by any suitable securement means.

The drive shaft 82 is arranged to be rotated about its longitudinal axis 34 at a high rate of speed to cause the concomitant rotation of the cutter tip 24. In order to support the drive shaft 82 at a central (neutral) position with the catheter tube along its length, irrespective of bends in the catheter up to a minimum radius of curvature, e.g., 3 inches, while also preventing the drive shaft from going into critical whirl, the flexible drive assembly 26 also includes an elongated bearing member 86. As can be seen, the bearing member 86 comprises a helical or spiral cylindrical coil of wire surrounding the flexible drive shaft 82. The sprial bearing extends substantially the entire length of the catheter from a proximately located point adjacent the motor (not shown) to the distal end 22 of the catheter.

As can be seen in FIG. 4 the outer diameter of the helical coil bearing 86 is sufficiently great so that its loops just clear the interior surface 88 of the catheter tube 44 to hold the bearing 86 securely centered in place therein. The inside diameter of the central passageway 90 extending down the length of the coil bearing 86 is just slightly greater than the outside diameter of the flexible drive shaft 82 so that the drive shaft 82 can rotate freely therein as shown by the arrows in FIG. 3.

As shown in FIG. 1 the distal end 92 of the coil bearing 86 is connected to a stationary disk-like wall retaining member 94 which is fixedly secured to the proximal end of the outer bushing 44. The wall 94 includes a central opening 96 therein and through which the flexible drive shaft 82 extends. The diameter of the opening 96 is sufficiently large to enable liquid which is introduced into the tubular space 98 within the catheter at the proximal end thereof to flow from that space through opening 96 and into the longitudinally extending passages 62 for egress from the interface 36. The securement of distal end 92 of the helical coil bearing 86 to the stationary wall 94 is effected by any suitable means, such as welding.

As will be appreciated by those skilled in the art inasmuch as the helical bearing surrounds the drive shaft 82 along its full length while keeping the drive shaft centered, the drive shaft is in effect held in position along its entire length and cannot thus go into critical whirl.

In order to insure that the catheter is sufficiently flexble to negotiate short radia of curvature, while not presenting an undue impediment to the flow of cooling fluid through the passageway 98 in the catheter, the diameter of the wire making up the helical coil and the pitch of the coils loop and the pitch of the helical coil bearig 86 are appropriately selected. In the embodiment shown and described herein the diameter of the wire making up the helical coil is approximately 0.01 inch (0.25 mm) and the pitch of each coil is approximately 45°. This construction optimizes bending, flexibility, torsional strength and fluid flow passage. It must be pointed out that the wire diameter and/or pitch of the helical bearing may be other dimensions, if desired, and depending upon the application. As will be appreciated of course, the shorter the pitch the more convolutions of the helix and hence the greater distance through which fluid must flow.

In accordance with the preferred embodiment of the catheter the helical coil bearing 86 is formed of a strong, yet flexible, low friction material, such as heat treated beryllium-copper.

It must be pointed out at this juncture that the drive shaft or wire 82 may be formed from multiple elements in lieu of the single wire of tube described heretofore. Thus, as shown in FIG. 9 the drive shaft can be a rope consisting of a central wire 82A surrounded by six helical wires 82B. Alternatively the central wire can be a tube 82C as shown in FIG. 10 surrounded by six helical wires 82B.

Referring now to FIG. 5 there is shown an alternative embodiment of a catheter for performing the various methods of this invention. The embodiment shown in FIG. 5 is denoted by the reference numeral 100 and is identical in many respects to the embodiment 20 disclosed heretofore. To that end all common features are given the same reference numerals as given with respect to embodiment 20. The major difference in the embodiment in FIG. 5 is that the catheter includes a central passageway extending down its length through which a conventional guide wire can pass to facilitate the placement of the catheter at the desired intravascular position. In order to make use of that central passageway the flexible drive assembly of the embodiment of FIG. 5 includes an elongated drive shaft, which as will be described in considerable detail later comprises a double helical coil having a longitudinally extending passageway therethrough and through which the guide wire can pass. Also, as can be seen in FIG. 5 the cutter tip of embodiment 100 is thread-mounted, as opposed to being pin mounted like that of the embodiment of FIG. 1.

Inasmuch as many of the features of the catheter 100 of FIG. 8 are the same as that described heretofore and using the same reference numerals, such parts will not be described in detail in the description of FIG. 5 to follow.

Disposed within the central passageway 58 of the inner bushing 56 is a cutter tip mounting shaft 102. The shaft 102 is an elongated cylindrical member having a central passageway 104 extending longitudinally therethrough. The distal end of the shaft 102 is denoted by the reference number 108 and extends beyond the front face 38 of the outer bushing. The projecting portion 108 includes helical threads 110 extending about the periphery thereof. A matingly threaded bore 112 extends into the cutter tip 24 and is arranged for threaded receipt of the projecting portion 108 of shaft 102 to mount the tip on the shaft. A central passageway 112 is also provided in the cutter tip 24 and is aligned with the passageway 104 in the tip mounting shaft 102. It is through the aligned passages 112 and 104 at the distal end of the catheter that the member (e.g., guide wire) forming the bearing surface for the drive shaft of the flexible drive assembly 26 passes. That guide wire used in the catheter 100 is denoted by the reference numeral 114, and can be of any conventional construction used to guide a catheter to an appropriate intravascular position.

As can be seen clearly in FIGS. 5 and 8 the flexible drive shaft 116 itself comprises a pair of cylindrical helical (spiral) wires which are interlaced with each other and which extend about the guide wire 114 for substantially the entire length of the catheter tube 42. The two helical wires forming the elongated drive shaft 116 are specifically denoted by the reference numerals 118 and 120, an each is fixedly secured at its distal end to the flanged end 106 of the cutter tip mounting shaft 102 by suitable means, e.g., weld joints 120.

As can be seen clearly in FIG. 8 the outside diameter of the interlaced coils making up the flexible drive shaft 116 are each slightly less than the inside diameter 88 of the catheter tube 42 to enable the drive shaft 116 to freely rotate about its central axis 34. Moreover, the two helical wires 118 and 120, when interleaved define a longitudinally extending central passageway 122 therethrough. The outside diameter of the passageway 122 is just slightly greater than the outside diameter of guide wire 114 to enable the two spiral wires 118 and 120 making up the drive shaft 116 to rotate as a unit about the guide wire. The proximal end of the flexible drive shaft 116 is connected by means (not shown) to be electric motor (not shown) to effect such rotation, and hence power the catheter 100.

As will be appreciated by those skilled in the art with the guide wire 114 in place it is centered in the catheter tube 42 by the passageway 104 at the distal end thereof and by appropriate centering means (not shown) at the proximal end thereof. Since the outer periphery of the coils making up the helical drive shaft 116 are spaced slightly from the inner surface of the catheter tube the shaft is enabled to rotate freely about the guide wire, while being centered within the catheter tube notwithstanding the fact that the tube 42 may bend around relatively sharp radia of curvature, e.g., 3" (76 mm). Moreover, inasmuch as the helical drive wires 118 and 120 are supported by the guide wire 114 passing therethrough along substantially the entire length thereof the drive shaft 116 formed by those wires is precluded from going into critical whirl, irrespective of the speed of rotation.

The rotation of the helical drive shaft 116 creates a pumping effect so that the cooling (lubricating) liquid introduced into the interior of the tubular catheter 42 at a proximal location is pumped down the length thereof. Accordingly, that liquid flows to the distal end of the catheter and through communicating passageway 62 and interface 36 out of the catheter contiguous with the tip 24. This action, is noted heretofore, has the effect of preventing snagging of the cutting tip while also insuring damage to the patients vascular system does not arise.

In accordance with the embodiment of the invention shown in FIG. 5 each of the wires 118 and 120 forming the flexible drive shaft 116 is of 0.01 inches (0.25 mm) outside diameter, with the pitch of each coil of the helix being approximately 45°. The inside diameter of the catheter tube 42 and its outside diameter is the same as described with reference to FIG. 1. Moreover the composition of the wires making up the flexible drive shaft 116 is also heat treated beryllium-copper.

It must be pointed out at this juncture that while the embodiment shown in FIG. 5 utilizes two helical wires to form the flexible drive shaft 116 such a construction is not required. Thus more than two wires can be used, providing that the wires are located so as to create a balanced load when driven by the motor.

It also must be pointed out at this juncture that in lieu of a single filament guide wire 114 a multi-filament wire or tube can be utilized. Moreover the guide wire itself can be formed as a spiral of filaments and/or tubes as shown in FIGS. 9 and 10, respectively.

The catheter 100 in FIG. 5 is arranged to be guided to its operative position within the artery or other lumen into which it is to be disposed by the use of the conventional guide wire 114. This action is accomplished by inserting the guide wire at the appropriate selected site in the body, such as into the femoral artery. The guide wire is then passed via the aorta into the coronary artery to the location of the restriction to be opened. The introduction of the guide wire can be aided by a fluoroscope, and a contrast medium can also be introduced into the artery. The catheter 100 is then threaded down the guide wire 114 via the opening 112 and 104 at the distal end thereof and through the central passageway extending down the helical drive shaft 116 until the tip 24 of the catheter is located immediately adjacent the proximal end of the restriction to be opened. As in the other embodiment a suitable liquid is then introduced into the interior of the catheter tube 42 from a point adjacent the proximal end thereof to aid in lubricating and cooling the moving components within the catheter. Moreover the rotation of the helical coil drive shaft results in the creation of a pumping action on the introduced liquid. Thus, the liquid is aided in flowing down the catheter to the distal end. The liquid flows into communicating passages 62 from whence it flows out of the open interface 36. As described earlier this exiting liquid applies positive pressure to the vessel wall to move the vessel wall slightly outward radially so that damage to the wall by the cutter head 24 does not occur. In addition the flow of liquid outward through the interface 36 also precludes any fiberous tissue from snagging in the cutter head.

In accordance with either embodiment of the catheter the liquid which is passed down the catheter can, if desired, be oxygenated to eliminate distal ischemia during the restriction opening procedure by the catheter. Also, if desired, nitrates, contrast media or other drugs can be added to the liquid as needed during the procedure.

As should now be appreciated the revascularization methods of this invention as well as the catheters as disclosed and claimed in the aforementioned copending applications enable coronary and peripheral (e.g. leg) revascularization of patients either intraoperatively or percutaneously, thereby providing methods of treatment which are less invasive, less expensive and less time consuming than prior art techniques. Moreover, the methods of this invention and the aforementioned catheters enable revascularization of smaller arteries and longer lesions than otherwise possible. Thus, with the instant invention one can prophylacticly treat coronary artery disease, perhaps one of the most widespread diseases affecting Americans. It will also be appreciated by skilled in the art that the subject method and the catheters as described can be readily utilized to remove a thrombosis in a manner similar to the restriction opening process.

The subject invention is also of significant utility for effecting tube or duct (such as eustachian tube, fallopian tube, etc.) dilation. With regard to the latter, a substantial number of women in the United States are infertile due to fallopian tube malfunction or stricture. At present there is no device or simple procedure to dilate or open the fallopian tube. In this connection while microsurgical procedures do attempt to alleviate the occlusion or stenosis, the results have been poor, the technique difficult, expensive and of limited availability. By utilizing the teachings of this invention a catheter, like those discussed herein can be passed via the cervical so to the fallopian tube to effect the dilation of the stenosis or occlusion in the same manner as described with reference to the revascularization of arteries.

As is known to those skilled in the art bypass surgery in the leg using the in situ approach for valvulecomies has proven superior to other methods to provide renewed blood circulation to the leg. However, in order to destroy or otherwise render inoperative the valves in the vein section so that the section can be used as an artery complex and lengthy surgical procedures are necessary. In this regard typical valvulecomies require complete exposure of the vein so that the valves thereof can be destroyed. Thus, heretofore in situ valvulecomies have been primarilarly confined to "above-the-knee" applications. In accordance with the teaching of the invention the catheters as discussed herein can be introduced into a vein section from a remote location and thereafter brought into contact with the valves to destroy the valves in a manner analgous to the revascularization of stenoic arteries. The advantage of such a method is that the vein need not be completely exposed and there is little danger of damage to the vein graft wall. Another significant advantage is that this technique can prepare veins for bypass to the level of an ankle and not merely in "above-the-knee" applications.

Kidney stones and other stones in the form of loose bodies having substantial calcium therein, e.g., gall bladder stones, bile stones, etc., affect the significant portion of the population in the United States and are the cause of great morbidity in those affected. Heretofore the techniques for removal of such stones have proven cumbersome, expensive and technically difficult to perform. While some apparatus such as the "Lithotripter" may prove a viable non-invasive approach to the removal or disintegration of such stones, such apparatus appears to be of limited applicability, i.e., will be available only at large medical centers which can afford the high costs involved. Moreover, use of the "Lithotripter" may not be applicable to destruction of all types of stones. In accordance with this invention a method is provided for effecting disintegration of hard bodily stones via the use of a flexible catheter like that disclosed and claimed herein and in the aforementioned copending, coassigned applications.

For example, in order to perform a cholecystecomy intraoperatively a flexible catheter such as set forth in the preferred embodiment to be described hereinafter, is introduced through the cystic duct into the common bile duct. The working head of the catheter is a rotary impacting member which is rotated at a high rate of speed and brought into engagement with the stone. Preferably means are provided in the catheter to insure that the stone is drawn toward the rotating working head. Such means will be described later, suffice for now to state that it creates a vortex fluid flow distally of the head to draw the stone toward working head. The rotation of the working head causes plural impacting surfaces to batter the stone, thereby pulverizing it. This action results in the disintegration of the stone to the point where the resulting particles are sufficiently small so that natural bodily functions may flush them from the body. The catheter is removed through the cystic duct, thereby maintaining the integrity of the common bile duct.

Referring now to FIGS. 11-14, the details of a catheter 200 having particular utility for effecting the disintegration of bodily stones or for accomplishing an in situ valvulectomy will now be described.

The catheter 200 in many respects is identical in construction to the catheters 20 and 100 described heretofore. Hence the same reference numerals will be used for the common components. In particular the drive means and bearing means for the drive means can be the same as in either catheter 20 or 100 (although as shown it is the same as catheter 20) whereas the working head 202 is considerably different. In this regard the working head basically comprises a propeller-like impacting member 204 having a pair of blades 204A and 204B. The member 204 is threadedly engaged onto a central mounting shaft 64 fixedly secured within an inner bushing 56. The inner bushing is disposed within an outer bushing 44. The outer bushing is fixedly secured within a tubular shroud 206. The distal end of the drive shaft or wire 82 is secured within the shaft 64, whereupon the shaft and the inner bushing to which it is connected are arranted to rotate about axis 34 under power from a remote motor (not shown). A plurality of slots 62 are provided along the inner bushing and serve as fluid passageways (to be described later).

The shroud 206 serves to protect the surrounding bodily tissue(s), e.g., duct walls, from damage caused by the rotary motion of the blades during the stone disintegration procedure. To that end the shroud is fixedly secured onto the distal end of the catheter tube 42 by a retaining band (not shown) like that described with reference to FIG. 1. As can be seen clearly in FIGS. 11 and 12, the shroud includes a plurality of generally rectangularly shaped windows or slots 208 disposed about the periphery thereof adjacent its distal end for reasons to be described later.

Each blade 204A and 204B of the impacting member 204 is curved and has a lead angle (FIGS. 12 and 13) arranged so that upon rotation of the member about the longitudinal axis 34 of the catheter in the direction of arrow 210 (FIG. 14) a toroidal vortex fluid flow path is induced distally of the working head. This vortex flow is denoted by the arrows 212 and is in the direction of the working head. This flow serves to draw the stone or venous valves to be acted upon by the catheter 200 into contact with the blades 204A and 204B. This in-drawing feature is of significant importance in applications wherein the stone or tissue to be destroyed is loose and not restrained by some body tissue, in order to ensure that the working does engage the stone or tissue to effect its destruction.

Figure 11:
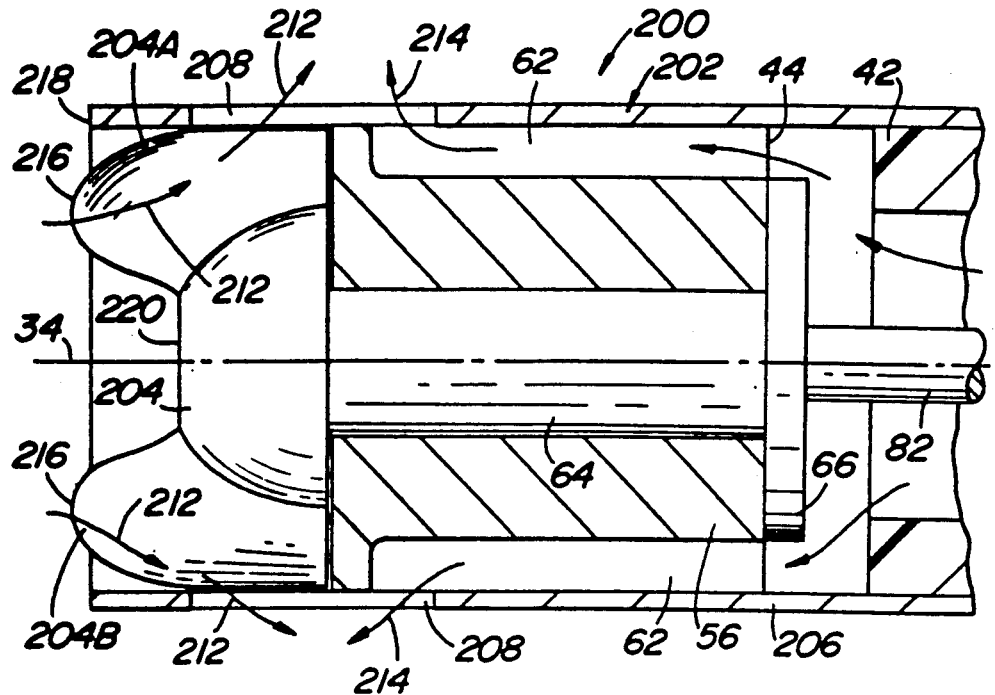
FIG. 11 is a side elevational view partially in section, showing the distal end of a catheter constructed in accordance with this invention and for carrying out the methods of this invention.

As can be seen in FIG. 11, the slots 62 are located between the bushing and the inner surface of the shroud 206 and serve as passageways enabling the fluid flowing through the interior of the catheter (and serving to cool and lubricate the moving components thereof as described with reference to the embodiments of FIGS. 1 and 5) to flow through the shroud's windows 208 out of the working head in the direction of arrows 214. The induced fluid flow distally of the head caused by the rotating blades also flows into the head and through the windows 208 (as shown by the arrows 212). These combined flows serve to push the duct walls or body tissue surrounding the stone away from the shroud 206, thereby aiding the shroud in protecting the patient from injury caused by the rotating blades.

Figure 12:
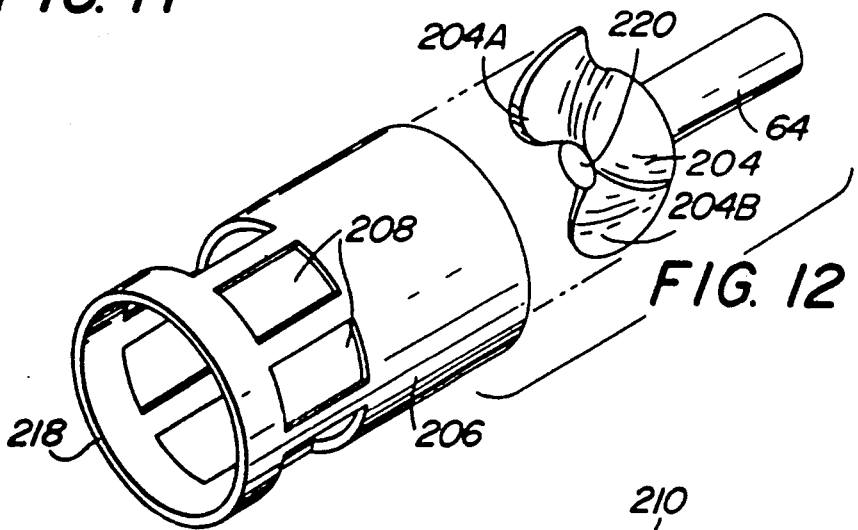
FIG. 12 is a reduced, exploded perspective view of a portion of the distal end of the catheter of FIG. 11.
Figure 13:
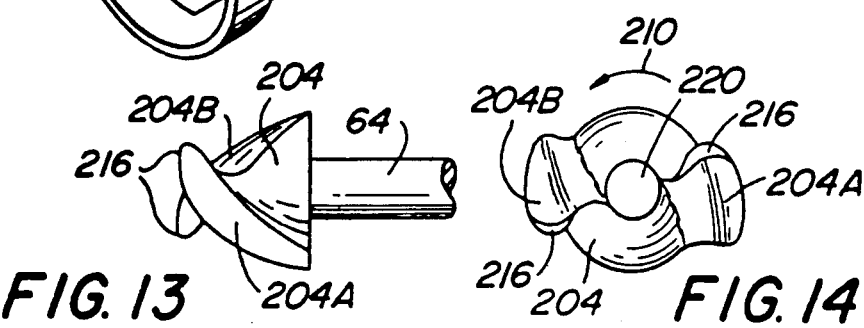
FIG. 13 is a reduced side elevational view of the impaction member forming a portion of the catheter of FIG. 11.
Figure 14:
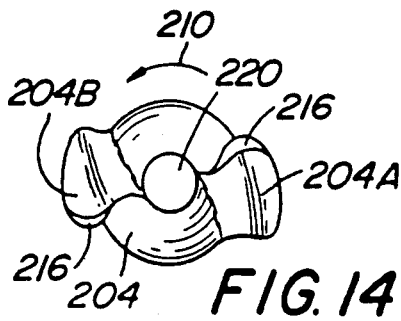
FIG. 14 is a front elevational view of the impaction member shown in FIG. 13.

As can be seen in FIG. 12 each blade tip is slightly rounded at 216 and projects a short distance, e.g., 0.005 to 0.010 inches, beyond the distal end 218 of the shroud 206. The rounded surfaces 216 serve as impact hammers to pulverize the stone upon contact therewith. In order to maximize the impact force the member 204 is relieved centrally at 220 so that the impaction surfaces 216 are located a substantial radial distance from the central axis 34 about which the member 204 rotates.

Operation of the catheter 200 to disintegrate a stone, such as a bile duct stone (not shown) is as follows. The catheter is introduced into an appropriate portion, e.g., the cystic duct, and then guided into the bile duct in which the stone is located and then until its working head is just proximately of the position of the stone. When the drive means is operated it causes the head 204 to rotate at a high rate of speed, e.g., 10,000 RPM or greater, thereby creating the vortex flow 218 which draws the stone into contact with the advancing head. The rapid rotation of the head 204 causes the impaction surfaces 216 to rapidly hammer away at the stone. This action pulverizes the stone, thereby resulting in its disintegration into particles of sufficiently small size as to be flushed from the duct by bodily fluids. The catheter is then withdrawn.

Operation of the catheter 200 to effect the in situ destruction of valves in a section of vein (not shown) is accomplished in a similar manner. Thus the advancement of the catheter distally, coupled with the vortex flow at the distal end thereof, draws the fragile valve elements of the vein into contact with the rotating blades 204A and 204B, whereupon the valve elements are destroyed or otherwise rendered inoperative. It should be noted that if the clearance between the blades and windows 208 is kept sufficiently small a shearing force results therebetween to aid in destroying the fragile valve elements.

It must be pointed out at this juncture that the catheter as disclosed and claimed herein and those disclosed and claimed in the aforementioned copending and commonly assigned applications can be used to effect the methods of this invention either intraoperatively, percutaneously or through any natural orifice in the body. Moreover, the power for effecting movement, e.g., rotation, of the working head can be produced by a wire drive arrangement like those shown and claimed in copending applications Ser. Nos. 06/701,063 and 06/746,220, or by a fluid drive system like that shown and claimed in copending applications Ser. Nos. 06/567,506 and 06/682,393, which are now U.S. Pat. Nos. 4,589,412 and 4,631,052 respectively.

It has been found that when the working head includes a rotating member, the rotation of the member during the advancement of the catheter through the body, e.g., artery, bile duct, etc., aids in the guidance of the catheter to the desired location. Thus, such catheters have a self guiding tendency to find the path of least resistance. Needless to say this feature further expedites the surgery involved by enabling precise and quick placement of the catheter.

It has also been found that a catheter like those of this and the aforegoing copending and coassigned applications can be utilized in accordance with another aspect of this invention to stop spasm (i.e., uncontrolled constriction) in an artery or other lumen and for preventing it from going back into spasm. To that end, a catheter is inserted into the artery in spasm and operated, as described heretofore, whereupon the spasm immediately ceases and remains stopped even after the catheter is removed. While this effect, i.e., the stoppage and prevention of spasm, results from the use of catheters in accordance with the method of this invention, the exact mechanism and exact physiologic reaction of the lumen to the action of the catheter is unknown at this time. For example, the operation of the working head may cause the same effects discussed with reference to lumen dilation to occur to stop and prevent spasm. More particularly, the action of the working head may cause permanent change, e.g., damage, to the neuromuscular juctions or muscle surrounding the lumen to prevent it from contracting.

The anti-spasm technique and method of this invention is not limited to arterial or vascular applications. Hence, this technique and method can be used in any application where spasm of a tubular body is a problem, e.g., bronchial tubes, the bowel, the exophagus, etc. To that end, this method can be used with any tubular structure which may go into spasm. Moreover, the diameter of the tubular structure in spasm can be substantially larger, e.g., more than double the diameter of the catheter with the anti-spasm procedure still being effective.

It should also be pointed out at this juncture that for applications wherein the working head is a rotating member including at least one blade defining a cutting edge, that edge should preferably be slightly rounded, e.g., have a radius in the range 0.001–0.005 inches, in the interest of maximizing arterial safety.

As should now be appreciated the subject invention provides a wide variety of non (or minimum) invasive surgical procedures. Those procedures specifically mentioned and discussed herein are by no means the only such procedures. Thus, other surgical procedures requiring access to an operative point from a remote location may also be accomplished using the methods and apparatus of this invention and the apparatus as disclosed and claimed in the aforementioned copending and coassigned applications, with such access being achieved either intraoperatively, percutaneously, or via a natural orifice.

Without further elaboration, the foregoing will so fully illustrate my invention that others may, by applying current or future knowledge, readily adopt the same for use under various conditions of service.

I claim:

1. The method of disentegrating a stone within the body of a living being by utilizing an elongated, small diameter, flexible catheter having a longitudinal axis and a distal end at which a working head is located, said working head being arranged for high speed movement with respect to said axis by associated drive means, said drive means arranged to freely effect the movement of said working head even if said catheter is bent through any arc up to a minimum radius of curvature and without resulting in excessive vibration which could interfere with the stone disentegration process, said method comprising inserting said catheter into said body from a remote location, causing said drive means to move said working head at a high rate of speed and advancing said catheter into contact with said stone along said axis as said working head is moving, whereupon the mechanical action of said moving working head causes the disentegration of said stone.

2. The method of claim 1 wherein said method additionally comprises the step of creating a path of fluid flow distally of said working head to pull said stone toward said head.

3. The method of claim 2 wherein said path of fluid flow is a vortex path.

4. The method of claim 1 wherein a liquid is injected into said body adjacent said working head to cooperate therewith in the disentegration of said stone.

5. The method of claim 4 wherein said injected liquid creates a path of fluid flow distally of said working head to pull said stone toward said head.

6. The method of claim 5 wherein said path of fluid flow is a vortex.

7. The method of claim 1 wherein said movement is rotary movement about said axis and wherein said rotary movement of said working head casues portions thereof to impact said stone at radially displaced positions from said axis to effect the pulverization of said stone.

8. The method of claim 7 additionally comprising a step of creating a path of fluid flow distally of said working head to pull said stone toward said head.

9. The method of claim 8 wherein said path of fluid flow is a vortex.

10. The method of claim 1 wherein said stone comprises a kidney stone, a gall stone, or a bile duct stone.

11. The method of claim 1 wherein said stone is located within a duct, passage or other lumen in said body.

12. Apparatus for disintegrating a stone within the body of a living being, said apparatus comprising an elongated, small diameter, flexible catheter having a longitudinal axis and a distal end at which a working head is located, said working head being arranged for high speed movement with respect to said axis by drive means located within said catheter, said drive means being arranged to freely effect the movement of said working means even if said catheter is bent through any arc up to a minimum radius of curvature and without resulting in excessive vibration which could interfere with the process, said working head comprising portions adapted to engage said stone at a high rate of speed to effect the destruction thereof.

13. The apparatus of claim 12 wherein said working head comprises a member adapted for rotation about said axis and including portions arranged to impact said stone at radially displaced positions from said axis.

14. The apparatus of claim 13 comprising shroud means mounted at the distal end of said catheter and covering said rotating member while allowing said impacting portions to extend therebeyond for engagement with said stone.

15. The apparatus of claim 12 additionally comprising means for creating a path of fluid flow distally of said working head to pull said stone towards said head.

16. The apparatus of claim 15 additionally comprising a shroud for covering said working head except for said impacting portions.

17. The apparatus of claim 12 additionally comprising bearing means extending within said catheter, one of said bearing and said drive means being formed as a spiral of at least one wire wrapped about the other of said means, whereupon said drive means can be rotated freely with respect to said other means to effect the movement of said working head, said drive means and said bearing means cooperating with each other to maintain the drive means in a neutral position within the catheter as the catheter is bent through any arc up to minimum radius of curvature while enabling said drive means to be rotated about said longitudinal axis at a high rotational speed without resulting in excessive vibration.

18. Apparatus for performing and in situ valvulectomy in the vein of a living being, said apparatus comprising an elongated, small diameter, flexible catheter having a longitudinal axis and a distal end at which a working head is located, said working head being arranged for high speed movement with respect to said axis by drive means located within said catheter, said drive means being arranged to freely effect the movement of said working head even if said catheter is bent through an arc up to a minimum radius of curvature and without resulting in excessive vibration which could interfere with the process, said working head comprising portions adapted to engage said valves at a high rate of speed to effect the destruction thereof.

19. The apparatus of claim 18 wherein said working head comprises a member adapted for rotation about said axis and including portions arranged to impact said valves at radially displaced positions from said axis.

20. The apparatus of claim 19 comprising shroud means mounted at the distal end of said catheter and covering said rotating member while allowing said impacting portions to extend therebeyond for engagement with said valves.

21. The apparatus of claim 18 additionally comprising means for creating a path of fluid flow distilly of said working head to pull said valve toward said head.

22. The apparatus of claim 21 additionally comprising a shroud for covering said working head except for said impacting portions.

23. The apparatus of claim 18 additionally comprising bearing means extending within said catheter, one of said bearing and said drive means being formed as a spiral of at least one wire wrapped around the other of said means, whereupon said drive means can be rotated freely with respect to said other means to effect the movement of said working head, said drive means and said bearing means cooperating with each other to maintain the drive means in a neutral position within the catheter as the catheter is bent through any arc up to a minimum radius of curvature while enabling said drive means to be rotated about said longitudinal axis at a high rotational speed without resulting in excessive vibration.

* * * * *

UNITED STATES PATENT AND TRADEMARK OFFICE
CERTIFICATE OF CORRECTION

PATENT NO. : 4,679,558
DATED : July 14, 1987
INVENTOR(S) : Kenneth Kensey and John Nash It is certified that error appears in the above-identified patent and that said Letters Patent are hereby corrected as shown below:

On the title page of the patent, in the address of the Assignee, please change "Telford, PA" to --Downington, Pa.--.

Signed and Sealed this

Fifth Day of April, 1988

*Attest:*

DONALD J. QUIGG

*Attesting Officer*      *Commissioner of Patents and Trademarks*